(12) United States Patent
Kohira et al.

(10) Patent No.: US 8,536,400 B2
(45) Date of Patent: Sep. 17, 2013

(54) ABSORBENT ARTICLE

(75) Inventors: Hiroshi Kohira, Tochigi (JP); Hiromi Tachikawa, Tochigi (JP); Hiroko Kawaguchi, Tochigi (JP)

(73) Assignee: Kao Corporation, Tokyo (JP)

( * ) Notice: Subject to any disclaimer, the term of this patent is extended or adjusted under 35 U.S.C. 154(b) by 1190 days.

(21) Appl. No.: 11/921,655

(22) PCT Filed: Jun. 7, 2006

(86) PCT No.: PCT/JP2006/311436
§ 371 (c)(1),
(2), (4) Date: Mar. 14, 2008

(87) PCT Pub. No.: WO2006/132279
PCT Pub. Date: Dec. 14, 2006

(65) Prior Publication Data
US 2009/0137975 A1 May 28, 2009

(30) Foreign Application Priority Data

Jun. 8, 2005 (JP) .................................. 2005-168300
Jun. 8, 2005 (JP) .................................. 2005-168301
Jun. 8, 2005 (JP) .................................. 2005-168302

(51) Int. Cl.
*A61F 13/15* (2006.01)

(52) U.S. Cl.
USPC .......................................... 604/360; 604/381

(58) Field of Classification Search
USPC ........................... 604/359–360, 378, 381–382
See application file for complete search history.

(56) References Cited

U.S. PATENT DOCUMENTS

| 5,439,734 | A | 8/1995 | Everhart et al. |
| 5,753,452 | A * | 5/1998 | Smith .............................. 435/14 |
| 5,795,921 | A | 8/1998 | Dyer et al. |
| 6,241,886 | B1 | 6/2001 | Kitagawa et al. |
| 6,812,169 | B2 | 11/2004 | Potts et al. |
| 7,160,949 | B2 * | 1/2007 | Ota et al. ....................... 525/242 |
| 7,314,752 | B2 * | 1/2008 | Kritzman et al. .......... 435/288.7 |
| 7,687,681 | B2 * | 3/2010 | Di Luccio et al. ............. 604/368 |
| 2002/0040210 | A1 * | 4/2002 | Luccio et al. .................. 604/367 |
| 2002/0065495 | A1 * | 5/2002 | Potts et al. ..................... 604/358 |
| 2003/0050618 | A1 | 3/2003 | Kondo et al. |

(Continued)

FOREIGN PATENT DOCUMENTS

| CN | 1171553 A | 1/1998 |
| CN | 1325314 A | 12/2001 |

(Continued)

OTHER PUBLICATIONS

Notice of Rejection dated Sep. 14, 2010 for Japanese Application No. 2005-168301.

(Continued)

*Primary Examiner* — Lynne Anderson
(74) *Attorney, Agent, or Firm* — Birch, Stewart, Kolasch & Birch, LLP (57) ABSTRACT

An absorbent article 1 including a blood separating member 4 capable of separating blood into blood cells and plasma. The blood separating member 4 preferably has pores with a diameter of 6 μm or smaller in a proportion of 20% to 90% in a pore size distribution measured in accordance with ASTM F361-86. A nonwoven fabric obtained by calendering a fiber aggregate can be used as the blood separating member.

10 Claims, 8 Drawing Sheets

(56) References Cited

U.S. PATENT DOCUMENTS

| | | |
|---|---|---|
| 2004/0007540 A1 | 1/2004 | Verpoort et al. |
| 2004/0067214 A1 | 4/2004 | Krautkramer et al. |
| 2004/0126543 A1 | 7/2004 | Potts et al. |

FOREIGN PATENT DOCUMENTS

| | | |
|---|---|---|
| EP | 0 800 082 A2 | 10/1997 |
| EP | 1 106 681 A1 | 6/2001 |
| JP | 5-264539 A | 10/1993 |
| JP | 9-143081 A | 6/1997 |
| JP | 10-31024 A | 2/1998 |
| JP | 10-512168 A | 11/1998 |
| JP | 11-197237 A | 7/1999 |
| JP | 2001-79067 A | 3/2001 |
| JP | 2001-348728 A | 12/2001 |
| JP | 2002-528232 A | 9/2002 |
| JP | 2003-175074 A | 6/2003 |
| JP | 2004-3073 A | 1/2004 |
| JP | 2004-505120 A | 2/2004 |
| JP | 2004-130085 A | 4/2004 |
| WO | WO-96/21682 A1 | 7/1996 |
| WO | WO 96/23474 | 8/1996 |
| WO | WO 00/25835 A1 | 5/2000 |
| WO | WO 02/00781 A2 | 2/2002 |

OTHER PUBLICATIONS

Notice of Rejection dated Sep. 21, 2010 for Japanese Application No. 2005-168302.

Notice of Rejection issued in corresponding Japanese Application 2005-168300 on May 25, 2010.

Notice of Rejection issued in corresponding Japanese Application 2005-168301 on Jan. 11, 2011.

Notice of Rejection issued in corresponding Japanese Application 2005-168302 on Jan. 11, 2011.

Extended European Search Report dated Mar. 4, 2011 for Application No. 06757143.0.

Japanese Office Action dated Jun. 14, 2011 issued in corresponding Japanese Patent Application No. 2005-168302 (with English translation).

Chinese First Office Action dated Dec. 21, 2010 issued in corresponding Chinese Patent Application No. 200680017797.X (with English translation).

\* cited by examiner

ABSORBENT ARTICLE

TECHNICAL FIELD

The present invention relates to an absorbent article with reduced rewet by menstrual blood (or blood).

BACKGROUND ART

Absorbent articles designed to absorb menstrual blood or blood, such as sanitary napkins, can allow menstrual blood, etc. absorbed by the absorbent member from the skin facing surface to pass back and rewet the wearer's skin due to pressure, which causes stickiness.

Methods that can be adapted to eliminate the stickiness problem include using an embossed sheet having a reduced skin contact area or bulky nonwoven fabric as a topsheet defining the skin facing side. However, the performance demands for absorbent articles have been increasing year by year, and such an improvement on the topsheet only would be insufficient to meet the current and growing demands.

JP 2001-348728A (document 1) discloses polyester microfiber useful as a web-forming material. Document 1 states that, because the microfiber is manufactured without using a diantimony trioxide catalyst, a web made of the microfiber requires no washing step for use as a blood separation filter, which is economically beneficial. In document 1 a sanitary product is mentioned as one of a variety of applications of the microfiber web. However, document 1 is silent on applying the microfiber web of the form with the blood-separating ability to a sanitary product.

JP 10-512168A (document 2) describes use of a polymer foamed material capable of absorbing blood or blood-based fluids as an absorbent member of a sanitary napkin. Document 2, however, gives no mention of blood separating ability.

DISCLOSURE OF THE INVENTION

The present invention provides, in its first aspect, an absorbent article including a blood separating member capable of separating blood into blood cells and plasma.

The present invention also provides, in its second aspect, an absorbent article including a liquid permeable topsheet, an absorbent core containing a fiber aggregate and a superabsorbent polymer, and the blood separating member interposed between the topsheet and the absorbent core.

The present invention also provides, in its third aspect, an absorbent article including a stack of a plurality of the blood separating members.

BRIEF DESCRIPTION OF THE DRAWINGS

FIG. 13(a) illustrates the action of a stack of a plurality of blood separating members, and FIG. 13(b) the action of a monolithic blood separating member with its weight per unit area being equal to that of the stack.

FIG. 15 illustrate a sanitary napkin according to still another preferred embodiment of the invention, in which FIG. 15(a) is a cross-section, FIG. 15(b) and FIG. 15(c) each show a pattern of through-holes of the blood separating member stack used in the napkin.

DETAILED DESCRIPTION OF THE INVENTION

The present invention will be described based on its preferred embodiments with reference to the accompanying drawing.

Figure 1:
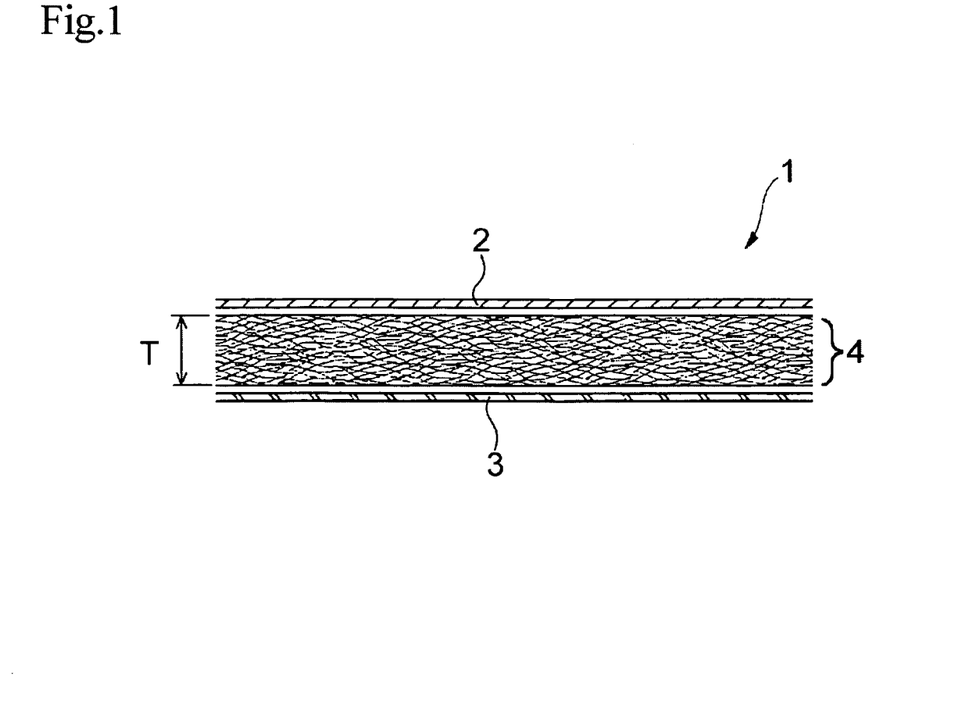
FIG. 1 is a cross-section of a sanitary napkin as a preferred embodiment of the present invention.

A sanitary napkin 1 as a preferred embodiment of the invention includes a liquid permeable topsheet 2, a liquid impermeable or water repellent backsheet 3, and an absorbent core 4 interposed between the sheets 2 and 3 as illustrated in FIG. 1. The absorbent core 4 is formed of a blood separating member capable of separating blood into blood cells and plasma.

The blood separating member used in the invention is a member having a function to separate blood into blood cells and plasma (also referred to as blood separating ability). Blood cells in blood are for the most part red cells. Hence, cell/plasma separation performed in the situation where blood is introduced into an absorbent article from its skin facing side is a phenomenon resulting from the fact that the three-dimensional region in which the red color of red cells spreads in the blood separating member is smaller than the region in which liquid components of blood spread. Accordingly, blood separation contemplated by the use of the blood separating member does not mean complete separation of blood into blood cells and plasma.

The blood separating members that are preferably used in the invention include those having pores with 6 µm or smaller diameter in a proportion of 20% to 90% in a pore size distribution measured in accordance with ASTM F361-86.

A red blood cell is a biconcave circular disk with a diameter of about 6 µm and a thickness of about 2 µm. It is preferred for the blood separating member to have at least a certain proportion of pores of 6 µm or smaller so as to trap such shaped red blood cells efficiently to display good blood separating ability. It is preferred that the blood separating member not have pores of 6 µm or smaller in a proportion of 100% so that satisfactory blood separation may be performed not only on the surface but in the inside of the blood separating member.

The proportion of pores with 6 μm or smaller diameter is more preferably 20% to 90%, even more preferably 30% to 80%.

A pore size distribution according to ASTM F316-86 is measured with, for example, Perm-Porometer CFP-1200-AEXL-ESA from Porous Material, Inc. In detail, a sample of about 10 to 15 mm diameter is prepared. The sample is soaked in a test fluid having a known surface tension, left to stand as soaked under reduced pressure of 20 mmHg or less for at least 15 minutes (usually about 20 to 30 minutes), and taken out to prepare a wet sample.

Figure 2:
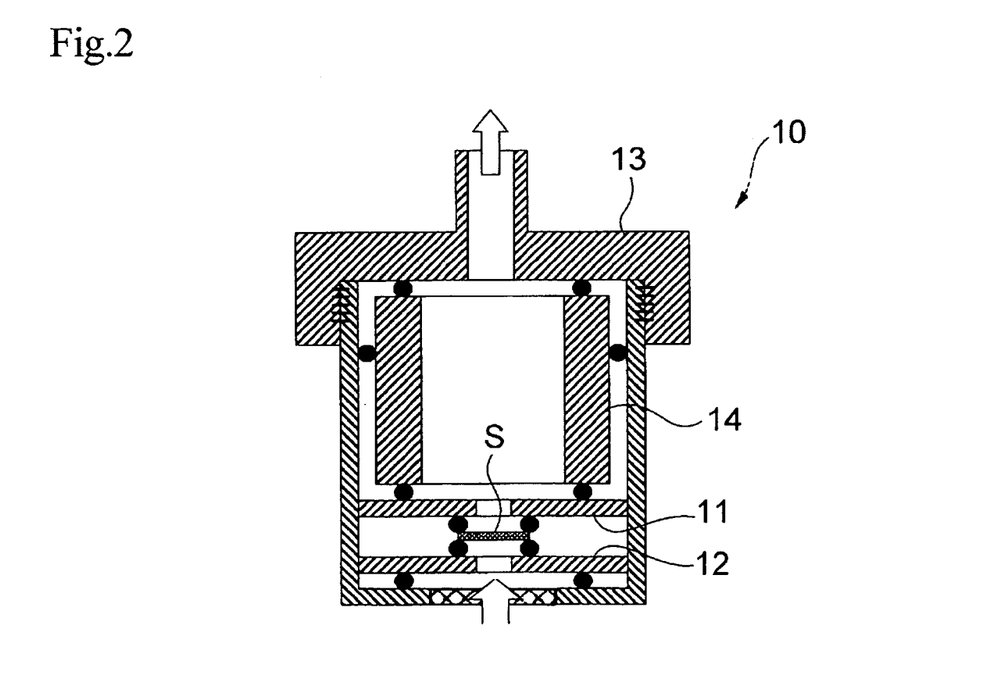
FIG. 2 schematically illustrates the instrument used to measure a pore size distribution and the manner of fixing a sample.

As illustrated in FIG. 2, the wet sample S is sandwiched between a pair of acrylic resin disks 11 and 12 each having a 3.3 mm diameter opening in the center, and the resin disks are set in a sample holder 10. A cap 13 is screwed to cause a cylinder 14 to press the disk 11, whereby the sample S is stably fixed. The black solid circles in FIG. 2 indicate rubber packing, which inhibits gas to flow through the gaps where it is disposed.

The holder 10 in which the wet sample S is fixed is set in the Perm Porometer. The inlet gas pressure on the bottom side of the holder 10 is raised at a constant rate ($1.4 \times 10^5$ Pa/min). Changes in gas pressure applied to the sample S and the flow rate of the gas from the holder 10 are recorded as exemplified by the graph of FIG. 3.

Figure 3:
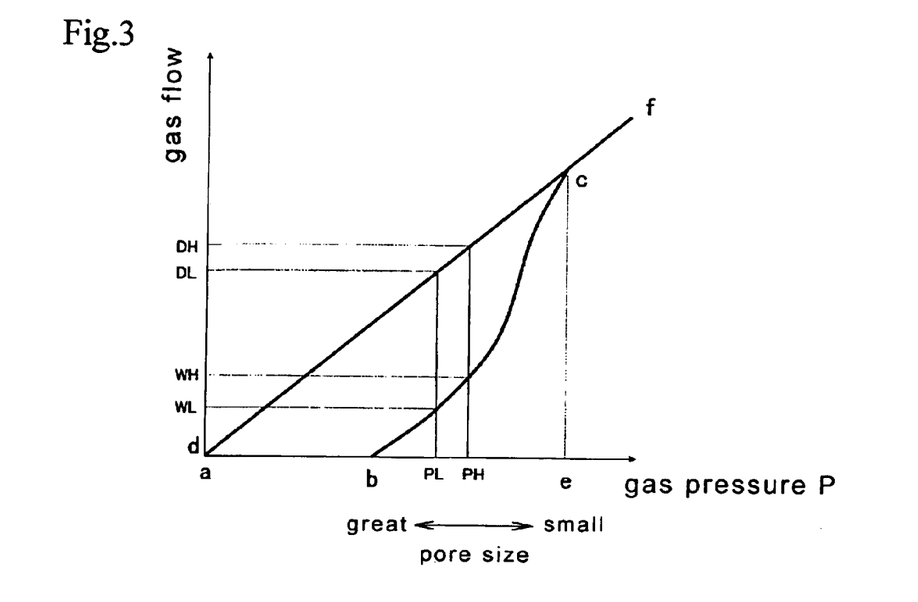
FIG. 3 is a graph showing changes in pressure and flow in pore size distribution measurement.

While the gas pressure on the sample S is low, no gas flow occurs as indicated by the nil between points a and b in FIG. 3. When the pressure reaches a certain point, gas begins to flow from the top of the holder 10. The pressure at which the first bulk gas flow is observed is called the bubble point (point b in FIG. 3), from which the maximum pore size of the sample is calculated. As the pressure increases further, the gas flow increases, depicting a curve according to the pore size distribution (the segment between points b and c in FIG. 3). Above a certain pressure, the increase in flow comes to be proportional to the increase in gas pressure to give a straight line (the segment from c to f in FIG. 3). The minimum pore size of the sample is calculated from the pressure e (point c in FIG. 3) at which the pressure vs. flow relation changes from the curve to the straight line.

The sample is regarded as having all the test fluid in the pores forced out and being in a dry state at the time point when the pressure vs. flow graph changes from a curve to a straight line. Then, the pressure applied to the sample S is decreased at a constant rate. The changes of the gas flow from the holder 10 vs. decreasing pressure on the sample S are similarly recorded.

In a dry sample, changes in gas flow are directly proportional to changes in gas pressure to give a straight relation between pressure and flow like the segment df.

A percentage of flow Q obtained in a specific pressure range (PL-PH) is calculated from the flow graph of the dry sample (segment df) and the flow graph of the wet sample (curve abc) by the formula:

$$Q (\%) = [(WH/DH) - (WL/DL)] \times 100$$

In the formula, (WH/DH) is a ratio of the air flow having passed through pores greater than the pore size corresponding to pressure PH to the air flow having passed through all the pores at pressure PH. Accordingly, a percentage of the number of pores greater than the pore size corresponding to pressure PH to total number of pores is calculated from that ratio. Likewise, (WL/DL) is a ratio of the air flow having passed through pores greater than the pore size corresponding to pressure PL to the air flow having passed through all the pores at pressure PL. Accordingly, a percentage of the number of pores greater than the pore corresponding to pressure PL to total number of pores is calculated from that ratio. The proportion of the number of the pores corresponding between pressures PL and PH in total number of pores can be calculated from the difference between these two ratios, (WH/DH)−(WL/DL).

The graph is divided into small increments of pressure in a range of from point b to point e, and Q is obtained for every increment to give a pore size distribution.

In Examples given later, the range between the pressure indicative of the maximum pore size (the pressure at point b in FIG. 3) and the pressure indicative of the minimum pore size (the pressure at point e in FIG. 3) is divided into equal increments corresponding to 2 μm pore size. To help recognize the midpoint of each class interval, the boundaries between class intervals are at integers (i.e., 2 μm, 4, 6, 8, . . . ). A pressure range lower than point b or higher than point e will be included in a class interval, which does not affect the value Q.

In the present invention, Galwick (16 mN/m) available from Porous Materials, Inc. was used as a wetting fluid having a known surface tension, and air dried by cold-compression (by use of DPKH-37 from Meiji Air Compressor Mfg. Co., Ltd.) was used as gas.

Figure 4:
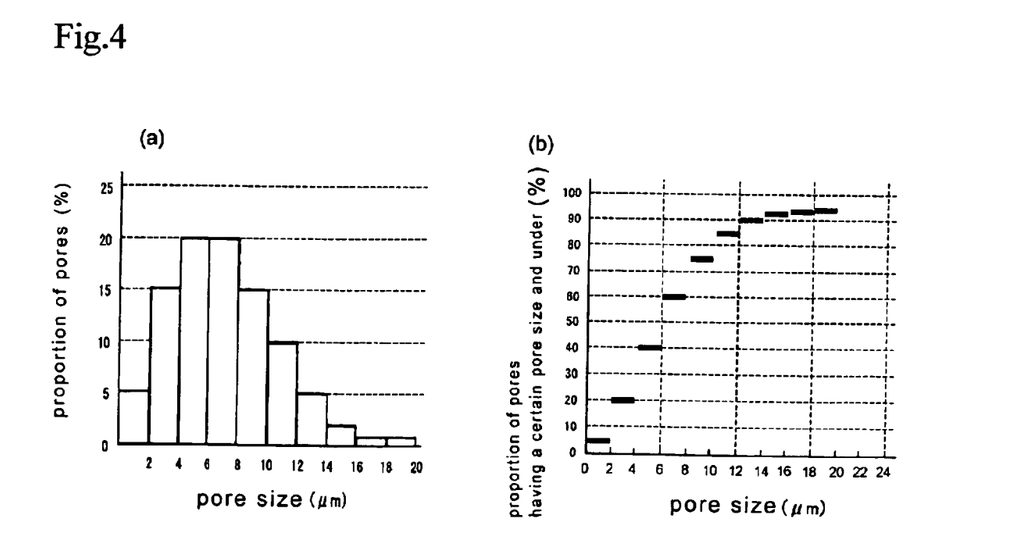
FIG. 4(a) a graph showing a pore size distribution measured in accordance with ASTM F316-86.
FIG. 4(b) is a graph showing the relation between pore sizes and proportions of undersize pores, prepared based on the measured pore size distribution.

FIG. 4(a) is a graph of pore size distribution measured in accordance with ASTM F316-86, in which the abscissa is pore size (μm), and the ordinate percentage of the number of pores as obtained from air flow having passed through the pores of a size. In Examples given infra, the Perm-Porometer was used to construct a histogram showing percentages of pores whose sizes fall within a range of every 2 μm increment (see FIG. 4(a)) and a graph as shown in FIG. 4(b), from which a proportion of pores of 6 μm or smaller was obtained.

FIG. 4(b) is a graph prepared based on the pore size distribution as shown in FIG. 4(a). In the graph of FIG. 4(b), the pore sizes (μm) are plotted as abscissa, and the proportion of the pores having a certain pore size and under as ordinate. In the particular example shown in FIG. 4(b), the value on the ordinate corresponding to a pore size of 6 μm is about 40%, which means that the proportion of the pores whose diameter is 6 μm or smaller is about 40%.

The sanitary napkin 1 of the present embodiment uses a blood separating member formed of a fiber aggregate.

A fiber aggregate having pores with 6 μm or smaller diameter in a proportion of 20% or more is obtained by, for example, calendaring a fiber aggregate made by melt blowing or a fiber aggregate made by using splittable fibers. As used herein, the term "fiber aggregate" is intended to include nonwoven fabric. Microfibers are obtainable by melt-blown spinning or by the division of splittable fibers, and a fiber aggregate suited for use as a blood separating member of the invention is obtainable by calendaring an aggregate of such microfibers. A blood separating member for use in the invention is also obtainable by calendaring a fiber aggregate made up of microfibers (fibers with an average diameter of 1 to 10 μm) prepared by other techniques.

The calendering as referred to herein is processing in which heat and pressure are applied to a fiber aggregate through calender rolls thereby to density the fiber aggregate. The number and arrangement of the calender rolls are not particularly limited. Examples of useful calender machines include I type or inclined three-roll calenders, I type, inverted L type, Z type or inclined Z type four-roll calenders, and Z type or L type five-roll calenders.

Calendering is preferably carried out under the following conditions.

The calendering temperature is preferably the softening point of the constituent fibers or lower. Calendering at temperatures higher than the softening point would cause fibers to adhere to each other, resulting in blocking the passageways for blood spread. The calendering pressure is not particularly limited as long as the proportion of the pores of 6 μm or smaller falls within the range from 20% to 90% measured in accordance with ASTM F316-86.

A splittable conjugate fiber is composed of at least two different resin components, in which each resin component is continuous in the fiber length direction, and the two or more resin components alternate in the circumferential direction of the fiber. The splittable fiber is splittable or separable into each resin component by a thermal and/or mechanical action. Splittable conjugate fibers that are capable of being divided into 4 to 32 split fibers are usable. The splittable conjugate fibers may be divided into individual resin components either prior to the calendering or by the calendering.

The fiber aggregate as a blood separating member is preferably made up of fibers having an average diameter of 3 to 30 μm. Diameters exceeding 3 μm secure certain strength of individual fibers and sufficient strength as a blood separating member. Fibers with diameters of 30 μm or smaller provide a blood separating member the stiffness of which gives no discomfort to a wearer when applied to a sanitary napkin or a like absorbent article. From these viewpoints, the average fiber diameter is more preferably 5 to 15 μm.

The average fiber diameter is measured as follows.

A fiber aggregate is frozen with liquid nitrogen and sliced with a sharp knife. The cut area is photographed at a magnification of 800 to 2000 times using a scanning electron microscope. The diameters of arbitrarily chosen ten fibers on the micrograph are measured using the scale bar of the micrograph and averaged.

The constituent fibers of the fiber aggregate as a blood separating member may be any of synthetic fibers, regenerated fibers (semi-synthetic fibers) or natural fibers. Synthetic fibers and/or regenerated fibers (semi-synthetic fibers) are preferred. Fibers of one or more thermoplastic polymers selected from polyester, polyamide, polyolefin, and ethylene-vinyl alcohol copolymers are particularly preferred in terms of fiber strength, cost, and processability.

The fiber aggregate as a blood separating member is preferably made mainly of hydrophilic fibers to develop a satisfactory blood separating ability. Such a fiber aggregate lets plasma of blood spread well, achieving good cell/plasma separation. A fiber aggregate made mainly of hydrophilic fibers exhibits improved liquid retentivity, which is advantageous for use as an absorbent core intended to absorb and contain a fluid as in the napkin 1 of the present embodiment.

Hydrophilic fibers include synthetic fibers having been hydrophilized with a hydrophilizing agent and regenerated fibers which are essentially hydrophilic. The hydrophilic fiber content in the fiber aggregate is preferably more than 50% up to 100% by mass, more preferably 70% to 100% by mass. Two or more kinds of hydrophilic fibers may be used in combination.

Synthetic fibers hydrophilized with a hydrophilizing agent are preferred hydrophilic fibers. The hydrophilizing agent to be used may be any of the type adhered to the fiber surface, the type kneaded into the resin material, and the type adhered to the fiber surface and partially fixed thereto, e.g., by heat treatment. The type adhered to the fiber surface and the type adhered and fixed to the fiber surface are preferred in terms of cost and processability. Hydrophilization by surface adhesion or surface adhesion followed by fixing can be achieved by, for example, immersing a fiber aggregate in an aqueous solution of a surface active agent (e.g., an anionic or nonionic surface active agent) or an aqueous solution of a hydrophilic polymer (e.g., polyvinyl alcohol, acrylamide, polyacrylic acid or an alkali metal salt thereof, or polyvinylpyrrolidone), followed by drying.

A fiber aggregate made mainly of hydrophilic fibers and containing hydrophobic fibers is also preferably used. The coexistence of hydrophobic fibers brings about improved liquid spread, allowing for effective use of a wider area of the blood separating member. The amount of rewet will further be reduced. It is preferred, nevertheless, that the content of the hydrophobic fibers in the fiber aggregate as a blood separating member be not more than 30% by mass, more preferably 20% by mass or less. Examples of useful hydrophobic fibers include synthetic fibers of thermoplastic polymers, such as polyester, polyamide and polyolefin, that are not hydrophilized. Two or more kinds of hydrophobic fibers may be used in combination.

In order that the fiber aggregate as a blood separating member may exhibit good blood separating ability and thereby achieve an appreciable effect on rewet reduction, the fiber aggregate preferably has a thickness T (see FIG. 1) of 0.3 mm or greater, more preferably 0.5 mm or greater, under a load of 49 Pa. The upper limit of the thickness is not particularly limited, being decided as appropriate in relation to absorption characteristics such as capacity required of the absorbent core. To prevent wearing discomfort, the thickness T is preferably 5.0 mm or smaller.

The thickness T is measured as follows. A 50 mm by 50 mm specimen is cut out of a fiber aggregate. A plate larger in size than the specimen and weighing 12.5 g is mounted on a measuring stage. The vertical position of the upper surface of the plate is taken as a base point A. The plate is once removed, the specimen is placed on the measuring stage, and the plate is again put thereon. The vertical position of the upper surface of the plate is taken as point B. The difference between points A and B is taken as the thickness of the fiber aggregate. Measurements are made with a laser displacement meter (CCD laser displacement sensor LK-080, from Keyence Corp.). A dial gauge type thickness meter will do in place of the displacement meter, in which case, too, the load applied to the specimen should be adjusted to 49 Pa.

The fiber aggregate as a blood separating member preferably has a basis weight of from 10 to 300 g/m$^2$, more preferably from 30 to 200 g/m$^2$, in terms of strength and flexibility.

Figure 5:
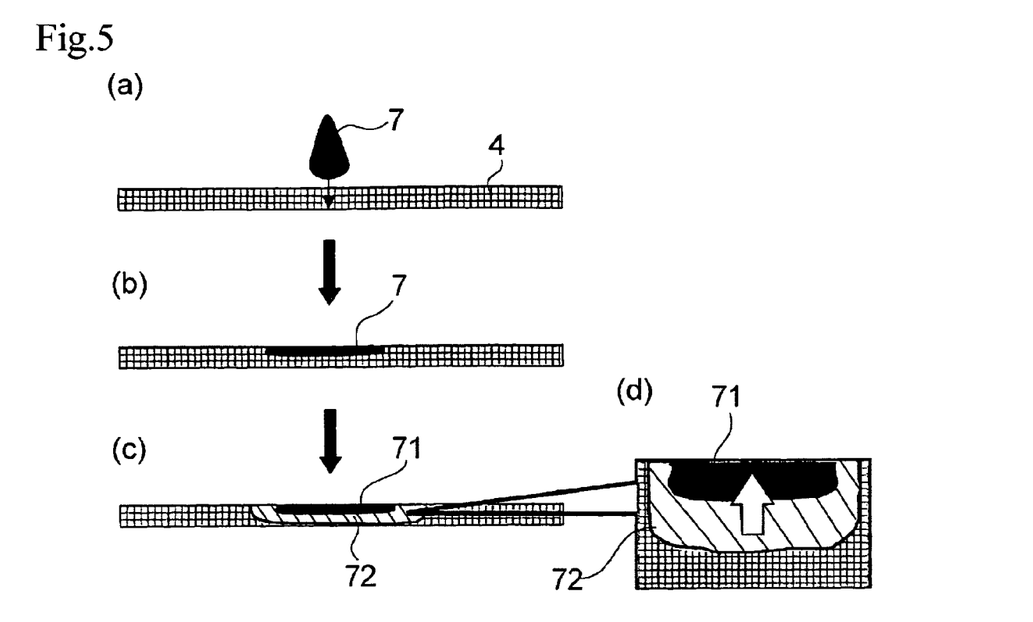
FIG. 5(a), FIG. 5(b), FIG. 5(c), and FIG. 5(d) illustrate the action of the blood separating member.

The sanitary napkin 1 of the present embodiment produces the following effects. Blood (menstrual blood) 7 supplied to the skin facing side (topsheet side) of the napkin 1 as illustrated in FIG. 5(a) passes through the topsheet (not shown) and is absorbed by a blood separating member constructing the absorbent core 4 as illustrated in FIG. 5(b). The blood (menstrual blood) 7 absorbed by the blood separating member is filtered and separated into blood cells 71 and plasma (liquid component) 72 in the blood separating member as depicted in FIG. 5(c). The plasma 72 spreads over a large area of the blood separating member, whilst the blood cells 71 spread over a relatively smaller area.

Since blood (menstrual blood) is separated into cells and plasma in the blood separating member, retransmission of the absorbed blood to the skin facing side of the napkin (the surface of the topsheet), namely rewet is greatly reduced.

The reason for this is believed to be as follows. As a result of blood filtration and separation in the blood separating member, a highly viscous layer having a markedly increased ratio of blood cells to plasma is formed near the topsheet side surface of the blood separating member as shown in FIG. 5(d), which layer blocks retransmission of plasma.

It is preferred that the blood separating member contain no superabsorbent polymer to provide an absorbent article with softness as a whole and improved comfort and fit.

Materials of other members constructing the sanitary napkin 1 are then described. The topsheet 2 and the backsheet 3 can be of any materials conventionally used in this type of absorbent articles. For example, nonwoven fabrics produced by various processes, perforated resin films, and composite laminates of these materials are useful as a topsheet. Thermoplastic resin films, water repellent nonwoven fabrics, and composite laminates of these materials, each of which may have or may not have moisture permeability, are useful as a backsheet.

Sanitary napkins of other embodiments of the present invention will then be described with reference to FIGS. 6 and 7. In what follows, the other embodiments will be described primarily with reference to differences from the above-described sanitary napkin. Elements and members common to the above embodiment are given the same numerals and will not be redundantly described. The description of the above sanitary napkin applies to these embodiments with the exceptions mentioned hereafter.

Figure 6:
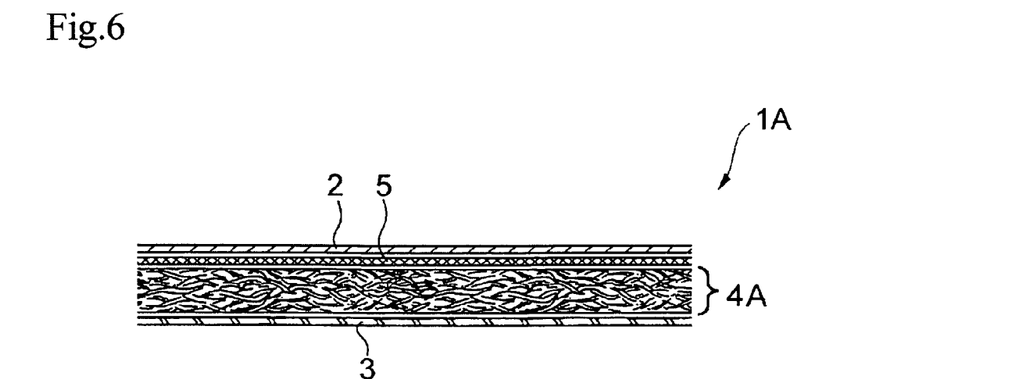
FIG. 6 is a cross-section of a sanitary napkin as another preferred embodiment of the invention.

A sanitary napkin 1A of FIG. 6 uses a blood separating member 5 formed of a porous resin film. The blood separating member formed of a porous resin film preferably has pores with 6 μm or smaller diameter in a proportion of from 20% to 90% in a pore size distribution measured in accordance with ASTM F361-86.

A resin film that satisfies the above condition is prepared by, for example, extruding a molten thermoplastic resin, e.g., polypropylene or polyethylene, loaded with a filler, e.g., calcium carbonate, stretching the resulting extruded film to make fine pores, and calendering the porous film. The amount of calcium carbonate to be mixed is preferably from 40% to 80% by mass. With a calcium carbonate content less than 40% by mass, fine pores would not be formed on stretching. With the content more than 80% by mass, the film may have reduced physical properties. A more preferred calcium carbonate content is from 50% to 70% by mass. Calcium carbonate preferably has an average particle size of from 0.1 to 10 μm. With a 0.1 μm or smaller particle size, calcium carbonate particles are liable to secondary agglomeration, which can result in a failure to mix with the thermoplastic resin uniformly. If the average particle size is more than 10 μm, large pores will be formed on stretching the film, resulting in a difficulty in creating a finely porous structure with pores of 6 μm or smaller in a proportion of at least 20%. A more preferred average particle size is from 0.5 to 5 μm. A stretch ratio is preferably from 1.5 to 5 times. At a stretch ratio less than 1.5 times, pores are not formed. At a stretch ratio more than 5 times, the film is apt to break. A more preferred stretch ratio is from 1.7 to 3 times. Stretching may be either uniaxial or biaxial but is preferably biaxial in view of film strength.

In the case where a porous resin film is used as a blood separating member, it is difficult to expect the film itself to serve for liquid retention. Hence, the sanitary napkin 1A has a commonly used absorbent core 4A disposed on the garment facing side of the porous resin film 5.

The absorbent core 4A may be any of various types that have been commonly used in this type of absorbent articles. For instance, a fiber aggregate made mainly of pulp fiber and containing or not containing a superabsorbent polymer may be used as an absorbent core 4.

As will be understood later, a sanitary napkin having, as an absorbent core 4A, a member having the same structure as an absorbent core 4A of a sanitary napkin 1C hereinafter described is a preferred embodiment of the second aspect of the present invention.

Figure 7:
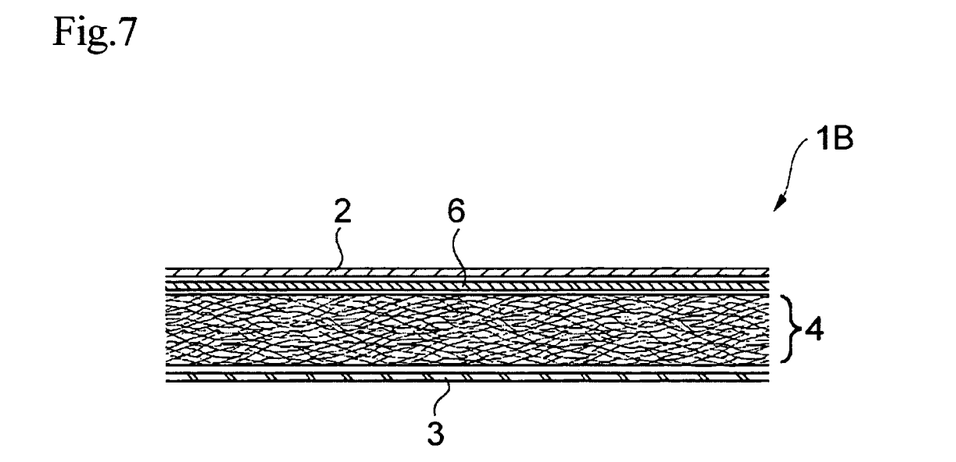
FIG. 7 is a cross-section of a sanitary napkin as still another preferred embodiment of the invention.

A sanitary napkin 1B of FIG. 7 has an intermediate sheet 6 between a topsheet 2 and a blood separating member as an absorbent core 4.

A blood separating member formed of a fiber aggregate has a dense structure and therefore tends to be slower in absorbing blood discharged onto the topsheet 2 than a conventional ordinary absorbent core formed of, e.g., an airlaid aggregate of pulp fibers. The absorption rate can be increased by disposing the intermediate sheet 6.

The intermediate sheet 6 must be such that allows blood discharged onto the topsheet 2 be quickly transmitted to the absorbent core 4. Any material, including nonwoven fabrics, having such a function or physical property can be used as the intermediate sheet 6 with no particular restriction. A nonwoven fabric useful as the intermediate sheet 6 is preferably made up of fibers whose fineness is from 1 to 10 dtex, more preferably from 2 to 7 dtex, and preferably has a thickness of from 0.3 to 1.0 mm, more preferably from 0.5 to 0.8 mm, under a load of 0.5 g/cm$^2$ (49 Pa) and a basis weight of from 10 to 50 g/m$^2$, more preferably from 20 to 40 g/m2.

Nonwoven fabrics formed by spunbonding, melt blowing, through-air bonding, and the like can be used as the intermediate sheet 6. A nonwoven fabric prepared by through-air bonding is preferred. The intermediate sheet 6 has pores of 6 μm or smaller in a proportion of 5% or less in a pore size distribution measured in accordance with ASTM F316-86.

A sanitary napkin 1C, a preferred embodiment of the second aspect of the invention, will be described with reference to FIG. 8. The description will proceed primarily with reference to differences from the sanitary napkin 1. Elements and members common to the sanitary napkin 1 are given the same numerals and will not be redundantly described. The description of the sanitary napkin 1 applies to the present embodiment with the exceptions mentioned hereafter.

Figure 8:
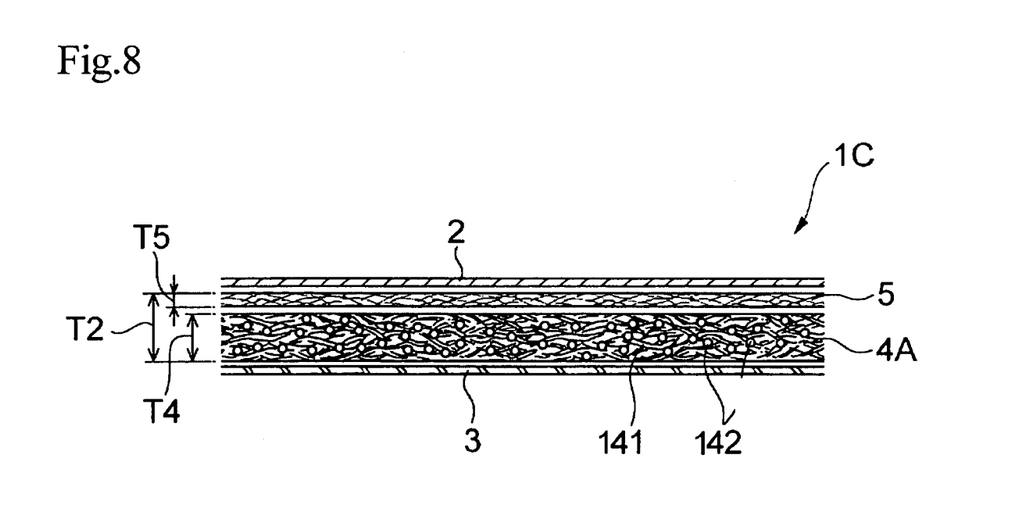
FIG. 8 is a cross-section of a sanitary napkin as a preferred embodiment of the invention (second aspect).

As illustrated in FIG. 8, the sanitary napkin 1C as a preferred embodiment of the second aspect of the invention includes a liquid permeable topsheet 2, a liquid impermeable or water repellent backsheet 3, and an absorbent core 4A interposed between the sheets 2 and 3. The sanitary napkin 1C further includes a blood separating member 5 capable of separating blood into blood cells and plasma between the topsheet 2 and the absorbent core 4A. The absorbent core 4A includes a fiber aggregate 141 and a superabsorbent polymer 142. The blood separating member 5 used in the sanitary napkin 1C is formed of a fiber aggregate.

The fiber aggregate as the blood separating member 5 preferably has a thickness T5 (see FIG. 8) of 0.3 mm or greater, more preferably 0.5 mm or greater, to exhibit a good blood separating ability and rewet reducing effect. While the upper limit of the thickness T5 is not particularly limited, it is preferably 5.0 mm to avoid giving discomfort to a wearer while the absorbent article is worn.

The absorbent core 4A preferably has a thickness T4 (see FIG. 8) of 0.5 mm or greater, more preferably 1.0 mm or greater, to obtain an absorption capacity enough to absorb the fluid having passed through the blood separating member 5. The upper limit of the thickness T4 is not particularly limited but is preferably 10 mm to avoid causing discomfort to a wearer while the absorbent article is worn.

The thickness T5 of the blood separating member preferably ranges from 1.0% to 90%, more preferably from 3% to 40%, of the total thickness T2 (see FIG. 8) of the blood separating member 5 and the absorbent core 4A.

The thicknesses T5 and T4 are measured as follows. A 50 mm by 50 mm specimen is cut out of the blood separating member 5 or the absorbent core 4A. A plate larger in size than the specimen and weighing 12.5 g is mounted on a measuring stage. The vertical position of the upper surface of the plate is taken as a base point A. The plate is once removed, the specimen is placed on the measuring stage, and the plate is again put thereon. The vertical position of the upper surface of the plate is taken as point B. The difference between points A and B is taken as the thickness of the blood separating member 5 or the absorbent core 4A. Measurements are made with a laser displacement meter (CCD laser displacement sensor LK-080, from Keyence Corp.). A dial gauge type thickness meter will do in place of the displacement meter, in which case, too, the load applied to the specimen should be adjusted to 49 Pa. Alternatively, the specimen may be placed between the measuring stage or a plate and another plate, and the cut area of the specimen is observed under a microscope or on an image to measure the thickness. The thicknesses T5 and T4 may also be measured on each of the blood separating member 5 and the absorbent core 4 separated from the sanitary napkin 1C by means of a laser displacement meter or a dial gauge type thickness meter or under a microscope or on an image.

The basis weight of the fiber aggregate as the blood separating member 5 is preferably from 10 to 300 $g/m^2$, more preferably from 30 to 200 $g/m^2$, in view of strength and flexibility.

The absorbent core 4A in the sanitary napkin 1C containing the fiber aggregate 141 and the superabsorbent polymer 142 absorbs and retains a fluid having passed through the blood separating member 5.

The fibers constituting the fiber aggregate 141 may be any of synthetic fibers, regenerated (semi-synthetic) fibers, and natural fibers, including polyester fibers (e.g., polyethylene terephthalate), polyamide fibers (e.g., nylon), polyolefin fibers (e.g., polyethylene and polypropylene), regenerated (semi-synthetic) fibers such as rayon and acetate rayon, pulp fiber, and cotton fiber. Conjugate fibers of synthetic fibers having a sheath/core configuration, a side-by-side configuration, etc. are also useful. These fibers may be used in combination of two or more thereof.

The superabsorbent polymer 142 may be of any kinds that have conventionally been used in this type of articles. In particular, those capable of absorbing at least 20 times their weight of liquid and becoming gel are preferred. Examples of such superabsorbent polymers include starch, crosslinked carboxymethyl cellulose, a homo- or copolymer of acrylic acid and an alkali metal salt thereof, polyacrylic acid or a salt thereof and a polyacrylate graft copolymer. These superabsorbent polymers can be used in combination of two or more thereof.

The superabsorbent polymer 142 may be present as dispersed almost uniformly in the fiber aggregate 141 or as localized in the thickness direction of the fiber aggregate 141, i.e., in the topsheet side, the backsheet side or intermediate therebetween. The superabsorbent polymer 142 may have the form of a layer sandwiched between adjacent fiber aggregate layers.

The fiber aggregate 141 may be either a web of loose fibers or a nonwoven fabric.

The content of the superabsorbent polymer 142 in the absorbent core 4A is preferably from 1.0% to 80% by mass, more preferably from 10% to 80% by mass, of the total mass of the absorbent core, in view of rewet reduction. A fiber to absorbent polymer ratio by mass is preferably 20:80 to 95:5, more preferably 25:75 to 90:10.

In the sanitary napkin 1C, the blood separating member 5 formed of the fiber aggregate is not wrapped in a cover sheet, such as tissue paper or a water permeable nonwoven fabric, while the absorbent core 4A is wrapped in a cover sheet, such as tissue paper or a water permeable nonwoven fabric.

Figure 9:
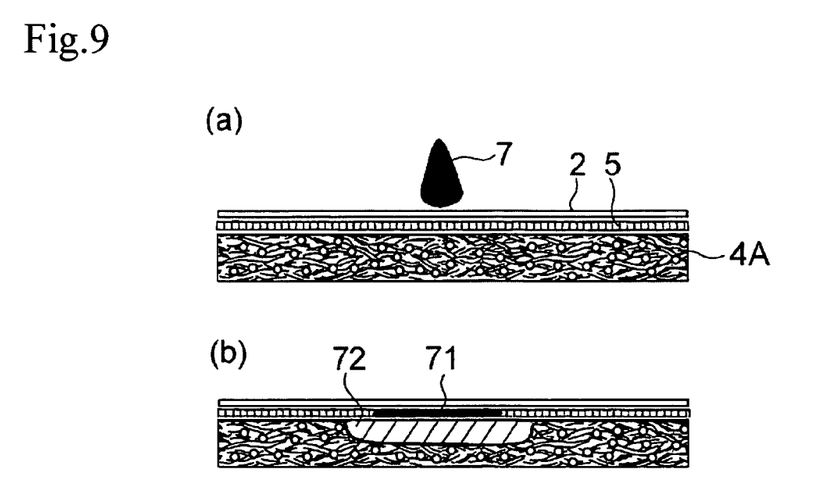
FIG. 9(a) and FIG. 9(b) illustrate the action of the blood separating member used in the invention (second aspect).

The sanitary napkin 1C of the present embodiment produces the following effects. Blood (menstrual blood) 7 supplied to the skin facing side (the side of the topsheet 2) of the napkin as illustrated in FIG. 9(a) passes through the topsheet 2. The liquid having passed through the topsheet 2 is filtered in the blood separating member 5 and separated into blood cells 71 and plasma (liquid component) 72 as depicted in FIG. 9(b). The plasma 72 is transmitted to the absorbent core 4A and absorbed and retained therein. On the other hand, the blood cells 71 are trapped in the blood separating member 5 and remain in and/or in the vicinity of the blood separating member 5.

In this way, blood (menstrual blood) is separated into blood cells and plasma in the blood separating member, whereby absorbed blood is prevented from retransmitted to the skin facing surface (the surface of the topsheet) of the sanitary napkin, that is, rewet is greatly reduced.

The reason for this is believed to be as follows. As a result of blood filtration and separation in the blood separating member, a highly viscous layer having a markedly increased ratio of blood cells to plasma is formed in the blood separating member 5 and/or its vicinity, which layer blocks retransmission of plasma. In addition, the superabsorbent polymer exhibits more effective absorptivity for the blood plasma with a reduced blood cell content as a result of separation of blood cells from discharged blood than discharged blood itself.

It is preferred that the blood separating member contain no superabsorbent polymer to provide an absorbent article with softness on its skin facing side and its vicinity and improved comfort and fit.

A sanitary napkin according to another embodiment of the second aspect of the present invention is described with reference to FIG. 10. The description will proceed primarily with reference to differences from the sanitary napkin 1C. Elements and members common to the sanitary napkin 1 are given the same numerals and will not be redundantly described. The description of the sanitary napkin 1C applies to the present embodiment with the exceptions mentioned hereafter.

Figure 10:
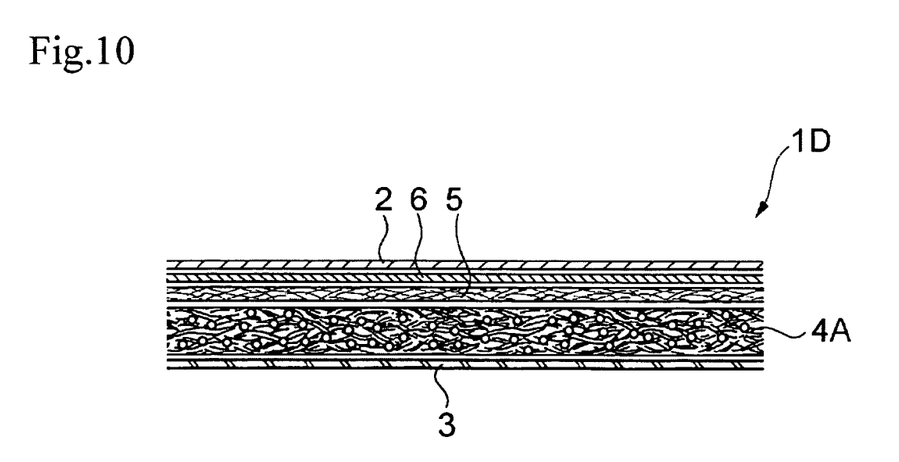
FIG. 10 is a cross-section of a sanitary napkin as another preferred embodiment of the invention (second aspect).

A sanitary napkin 1D shown in FIG. 10 has an intermediate sheet 6 disposed between a topsheet 2 and a blood separating member 5 formed of a fiber aggregate.

A blood separating member formed of a fiber aggregate has a dense structure and therefore tends to be slower in absorbing blood discharged onto the topsheet 2 than a conventional ordinary absorbent core formed of, e.g., an airlaid aggregate of pulp fibers. The absorption rate can be increased by disposing the intermediate sheet 6.

The intermediate sheet 6 must be such that allows blood discharged onto the topsheet 2 be quickly transmitted to the absorbent core 4A.

Any material, including nonwoven fabrics, having such a function or physical property can be used as the intermediate sheet 6 with no particular restriction.

A sanitary napkin 1E, a preferred embodiment of the third aspect of the invention, will be described with reference to FIG. 11. The description will proceed primarily with reference to differences from the sanitary napkin 1. Elements and members common to the sanitary napkin 1 are given the same numerals and will not be redundantly described. The description of the sanitary napkin 1 applies to the present embodiment with the exceptions mentioned hereafter. A number of the blood separating members each formed of a fiber aggregate according to the invention may be stacked one on top of another to make a multilayer absorbent core as in the present embodiment.

Figure 11:
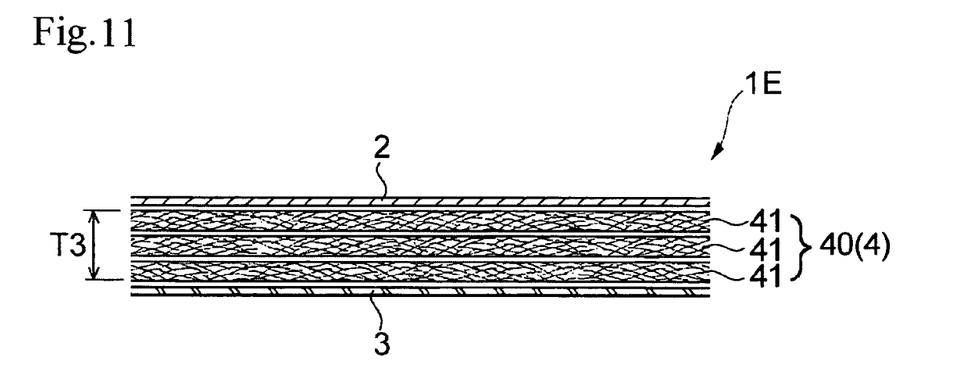
FIG. 11 is a cross-section of a sanitary napkin as a preferred embodiment of the invention (third aspect).

As illustrated in FIG. 11, the sanitary napkin 1E as a preferred embodiment of the third aspect of the invention includes a liquid permeable topsheet 2, a liquid impermeable or water repellent backsheet 3, and an absorbent core 4 interposed between the sheets 2 and 3. The absorbent core 4 is formed of a blood separating member stack 40 composed of a plurality of blood separating members 41 (three blood separating members in the illustrated example) each capable of separating blood into blood cells and plasma.

In the sanitary napkin 1E, the plurality of the blood separating members 41 stacked one on top of another are each formed of a fiber aggregate.

The fiber aggregate as a blood separating member is preferably made mainly of hydrophilic fibers to develop satisfactory blood separating ability. Such a fiber aggregate lets plasma of blood spread well, achieving good cell/plasma separation.

Furthermore, a fiber aggregate made mainly of hydrophilic fibers exhibits improved liquid retentivity, which is advantageous for use as an absorbent core as in the above-described napkin 1 or in the napkin 1E of the present embodiment.

As stated previously, a fiber aggregate made mainly of hydrophilic fibers and containing hydrophobic fibers is also preferred. The hydrophobic fibers may be present in all or part of the blood separating members 41 that constitute the stack 40 and are preferably present in at least the blood separating member 41 nearest to the skin facing surface.

In order that the stack 40 composed of a plurality of blood separating members 41 may exhibit good blood separating ability and thereby achieve an appreciable effect on rewet reduction, each blood separating member 41 preferably has a thickness of 0.3 mm or greater, more preferably 0.5 mm or greater.

The thickness T3 (see FIG. 11) of the blood separating member stack 40 is not particularly limited, being decided as appropriate in relation to absorption characteristics such as capacity required of the absorbent core. To prevent wearing discomfort, the thickness T3 is preferably from 0.6 to 10 mm, more preferably from 0.8 to 5 mm.

The thickness T3 is measured as follows. A 50 mm by 50 mm specimen is cut out of a blood separating member stack. A plate larger in size than the specimen and weighing 12.5 g is mounted on a measuring stage. The vertical position of the upper surface of the plate is taken as a base point A. The plate is once removed, the specimen is placed on the measuring stage, and the plate is again put thereon. The vertical position of the upper surface of the plate is taken as point B. The difference between points A and B is taken as the thickness of the stack. Measurements are made with a laser displacement meter (CCD laser displacement sensor LK-080, from Keyence Corp.). A dial gauge type thickness meter will do in place of the displacement meter, in which case, too, the load applied to the specimen should be adjusted to 49 Pa.

The blood separating members 41 each preferably have a basis weight of from 10 to 300 g/m$^2$, more preferably from 30 to 200 g/m$^2$, in terms of strength and flexibility.

The sanitary napkin 1E of the present embodiment produces the following effects. Since the blood separating members 41 are disposed on the garment facing side of the liquid permeable topsheet 2, blood (menstrual blood) 7 supplied to the skin facing side (topsheet side) of the napkin 1E as illustrated in FIG. 12(a) passes through the topsheet (not shown) and is absorbed by the blood separating member 41 constructing the stack as illustrated in FIG. 12(b). The blood (menstrual blood) 7 absorbed by the blood separating member 41 is filtered and separated into blood cells 71 and plasma (liquid component) 72 in the blood separating member as depicted in FIG. 12(c). The plasma 72 spreads over a large area of the blood separating member, whilst the blood cells 71 spread over a relatively smaller area.

Figure 12:
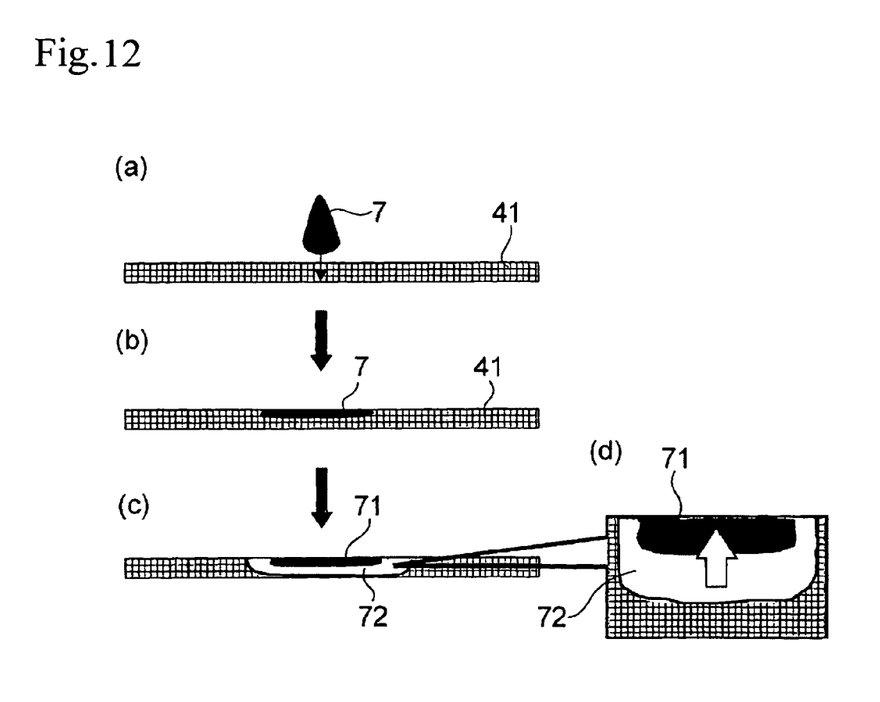
FIG. 12(a), FIG. 12(b), FIG. 12(c), and FIG. 12(d) illustrate the action of the blood separating member used in the invention (third aspect).

Since blood (menstrual blood) is separated into cells and plasma in the blood separating member 41, retransmission of the absorbed blood to the skin facing side of the napkin (the surface of the topsheet), namely rewet is greatly reduced.

The reason for this is believed to be as follows. As a result of blood filtration and separation in the blood separating member, a highly viscous layer having a markedly increased ratio of blood cells to plasma is formed near the topsheet side surface of the blood separating member as shown in FIG. 12(d), which layer blocks retransmission of plasma.

Figure 13:
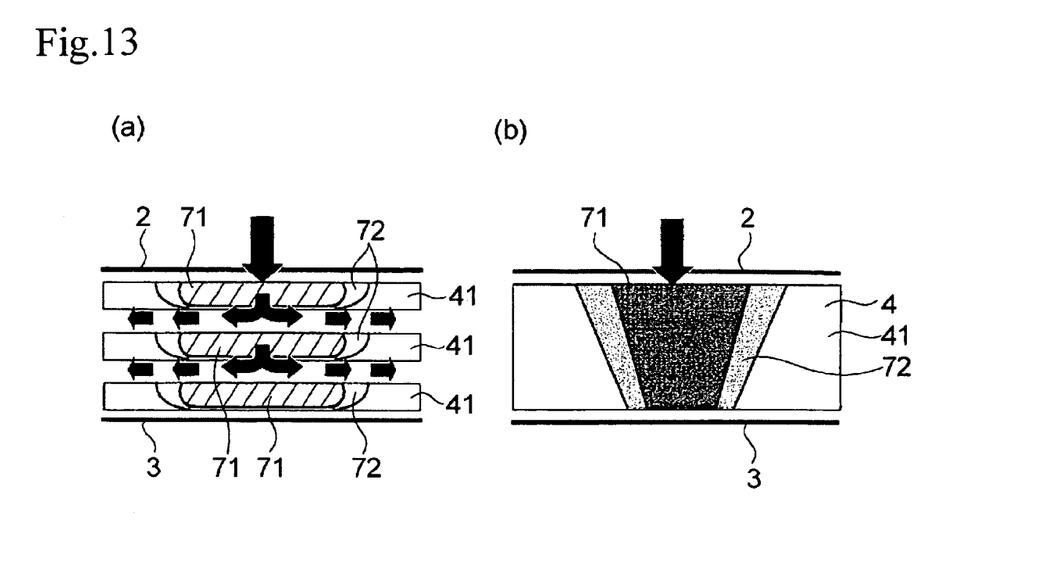

In addition, since the sanitary napkin 1E of the present embodiment has a plurality of the blood separating members with blood separating ability stacked one on top of another, in the case when a relatively large amount of menstrual blood (blood) is discharged (supplied) on the skin facing side, part of the blood penetrates the blood separating member 41 to reach a gap between two blood separating members 41 and flows through the gap to spread in the planar directions rapidly as illustrated in FIG. 13(a).

Thus, the blood separating member stack can be made effective use of over a wide planar range even in the inside of its thickness to provide improved filtration efficiency and further reduction of rewet. Blood is retained also in the gaps between blood separating members, which means that the blood separating member stack is capable of retaining more blood than the saturation limit of the material.

FIG. 13(b) represents an absorbent core formed of a monolithic single blood separating member. The planar area in which the blood separating function is performed decreases relatively steeply from the side of the topsheet 2 (skin facing side) toward the side of the backsheet 3 (the garment facing side). As a result, even with the weight per unit area being equal, the blood separating member stack according to the present invention has a larger blood absorption capacity and causes less rewet than such a monolithic blood separating member.

It is preferred that at least the blood separating member of the stack nearest to the skin facing surface of the napkin 1E be free from a superabsorbent polymer. It is more preferred that the whole stack of blood separating members be free from a superabsorbent polymer. Containing no superabsorbent polymer makes the absorbent article soft as a whole and provides improved wearing comfort and fit.

Sanitary napkins according to other preferred embodiments of the present invention will then be described with reference to FIGS. 14 through 16. In what follows, the embodiments will be described primarily with reference to differences from the above-described sanitary napkin 1E. Elements and members common to the napkin 1E are given the same numerals and will not be redundantly described. The description of the sanitary napkin 1E applies to these embodiments unless otherwise mentioned hereafter.

Figure 14:
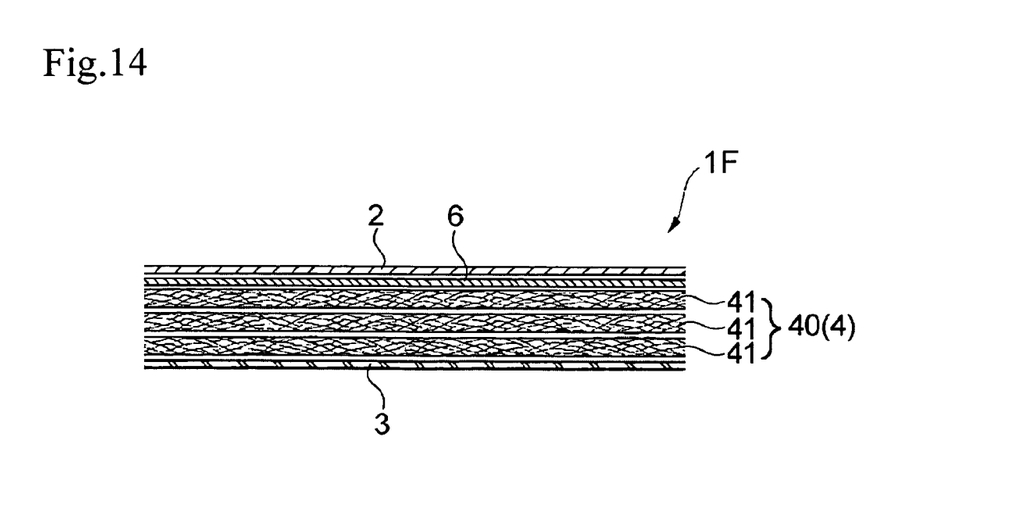
FIG. 14 is a cross-section of a sanitary napkin as another preferred embodiment of the invention.

A sanitary napkin 1F shown in FIG. 14 includes a topsheet 2, an absorbent core 4 formed of a stack 40 of a plurality of blood separating members 41, and an intermediate sheet 6 interposed between the topsheet 2 and the absorbent core 4.

A blood separating member formed of a fiber aggregate has a dense structure and therefore tends to be slower in absorbing blood discharged onto the topsheet 2 than a conventional ordinary absorbent core formed of, e.g., an airlaid aggregate of pulp fibers. The absorption rate can be increased by disposing the intermediate sheet 6.

The intermediate sheet 6 must be such that allows blood discharged onto the topsheet 2 be quickly transmitted to the absorbent core 4. Any material, including nonwoven fabrics, having such a function or physical property can be used as the intermediate sheet 6 with no particular restriction. Materials that are preferably used to form the intermediate sheet 6 are the same as those recited above as for the intermediate sheet used in the sanitary napkins 1B and 1D. The sanitary napkin 1D is structurally the same as the sanitary napkin 1C, except for having the intermediate sheet 6.

Figure 15:
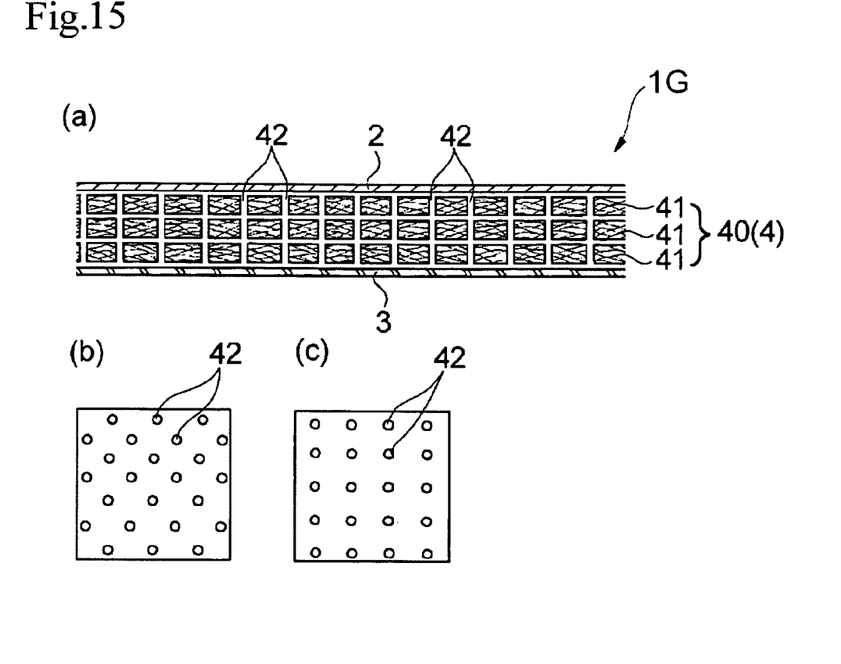
Figure 16:
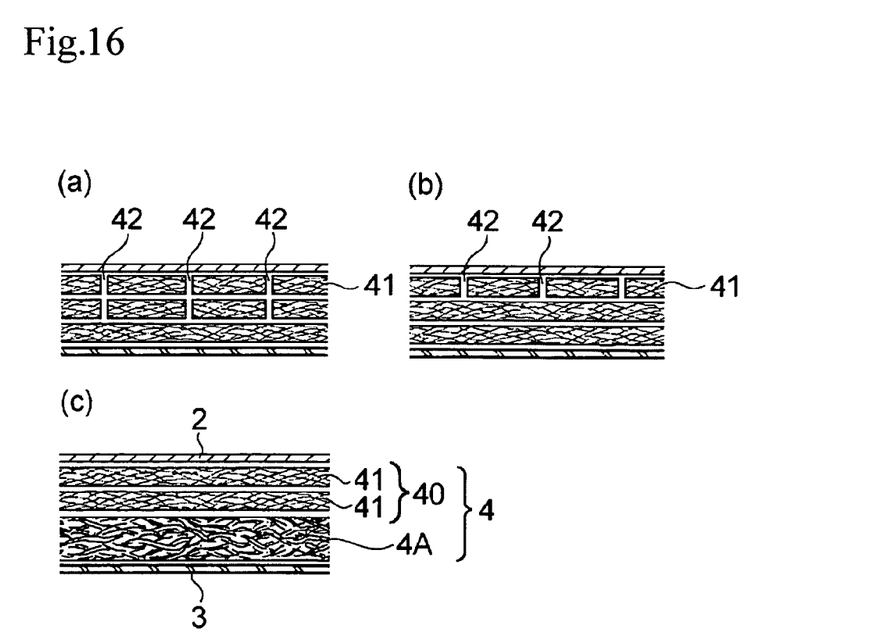
FIG. 16(a), FIG. 16(b), and FIG. 16(c) are each a cross-section of a sanitary napkin according to yet another preferred embodiment of the invention.

A sanitary napkin 1G illustrated in FIG. 15 has an absorbent core 4 formed of a stack 40 of a plurality of fiber aggregates as blood separating members 41 similarly to the sanitary napkin 1E. The difference resides in that through-holes 42 are made in the stack 40 to penetrate the total thickness of the blood separating members 41.

A blood separating member 41 formed of a fiber aggregate has a dense structure and therefore tends to be slower in absorbing blood discharged onto the topsheet 2 than a conventional ordinary absorbent core formed of, e.g., an airlaid aggregate of pulp fibers. The absorption rate can be increased by making such through-holes 42.

The individual through-holes 42 formed in the blood separating members 41 preferably have an opening diameter of 0.5 to 5 mm, more preferably 1 to 3 mm and are preferably arranged at a spacing of 0.5 to 8 mm, more preferably 1 to 5 mm.

FIGS. 15(*b*) and 15(*c*) are each a partial plan of the blood separating member 41 having through-holes 42 drilled therethrough as seen from the skin facing side thereof. The through-holes 42 can be arranged in a staggered pattern as in FIG. 15(*b*), in a square lattice pattern as in FIG. 15(*c*), or in any other various patterns.

The present invention is not limited to the aforementioned embodiments, and various changes and modifications can be made therein as exemplified as follows.

The single layer (monolithic) blood separating member or the multilayer blood separating member (i.e., the stack of blood separating members) may be combined with a conventional absorbent member such as an airlaid pulp fiber aggregate to provide an absorbent core for use in the invention. A blood separating member formed of a porous resin film and a blood separating member formed of a fiber aggregate may be used in combination.

In the second aspect of the invention, the blood separating member and the absorbent core may be bonded to each other in parts or may not be bonded at all.

While the number of the blood separating members stacked one on top of another is three in the examples illustrated in the drawing, it may be two or four or even more. It is preferably about 3 to 8.

In the case where through-holes are drilled through the stack of blood separating members, the holes may be drilled through only any one or two of the blood separating members. For example, through-holes may be formed through only one or two blood separator members nearest to the skin facing surface as illustrated in FIG. 16(*a*) or 16(*b*).

The blood separating member stack 40 may be combined with a conventional absorbent core such as an airlaid pulp fiber aggregate to provide an absorbent core for use in the invention. For example, the absorbent core 4 of the sanitary napkin illustrated in FIG. 16(*c*) has a stack 40 of two blood separating members 41 superposed on an absorbent core 4A having a conventional common structure. Various structures of absorbent cores that have been employed in this type of absorbent articles are usable as the absorbent core 4A, including a fiber aggregate made mainly of pulp fiber which may contain a superabsorbent polymer.

A blood separating member formed of a porous resin film may be used as a member constituting a blood separating member stack 40. The blood separating member formed of a porous resin film preferably has pores with 6 µm or smaller diameter in a proportion of 20% to 90% in a pore size distribution measured in accordance with ASTM F361-86.

The blood separating member may be located over the entire absorbent area of a sanitary napkin or in only a target region facing a body point of menstrual blood discharge. It is also possible to locate the blood separating member off the center to either end (front or rear end) or to either side (right or left) of a sanitary napkin.

The blood separating member formed of a fiber aggregate may or may not be wrapped in tissue paper or water permeable nonwoven fabric. The absorbent article may be of the type in which the blood separating member formed of a fiber aggregate is disposed between a liquid permeable topsheet and a liquid permeable backsheet.

The two or more blood separating members constituting the blood separating member stack may be bonded to each other in part or may not be bonded at all. The stack may or may not be wrapped in tissue paper or water permeable nonwoven fabric.

The term "absorbent article" according to the present invention includes not only sanitary napkins but bandages, dressings for injuries and wounds, surgical drapes or sheets, and the like.

EXAMPLES

The present invention will now be illustrated in greater detail by way of Examples, but it should be understood that the invention is not construed as being limited thereto.

Example 1

A nonwoven fabric having an average fiber diameter of 10 µm and a basis weight of 30 g/m$^2$ was formed by melt blowing polypropylene (PP) and calendered at a temperature of 40° C. and a linear pressure of 250 kgf/cm. The calendered nonwoven fabric was soaked in a 0.05% aqueous solution of a surface active agent (Mydol 10 from Kao Corp.) and dried spontaneously to give a test nonwoven fabric.

The resulting test nonwoven fabric was analyzed for pore size distribution in accordance with the method described above to find that the proportion of pores of 6 µm or smaller was 20%. The test nonwoven fabric was cut into a piece of 6 cm wide and 15 cm long, which was used as a blood separating member. A sanitary napkin was made by interposing the resulting blood separating member between the topsheet and backsheet taken out of a commercially available sanitary napkin Laurier Sarasara Cushion (for day use) available from Kao Corp.

Example 2

A sanitary napkin was made in the same manner as in Example 1, except for interposing the same blood separating member (test nonwoven fabric) as used in Example 1 and, as an intermediate sheet, an air-through nonwoven fabric weighing 40 g/m$^2$ between the topsheet and the backsheet. The intermediate sheet was on the topsheet side, and the blood separator member on the backsheet side.

Example 3

A web having a basis weight of 60 g/m² was formed using 16-segmented splittable fibers composed of polypropylene (PP) and polyethylene (PE). The web was formed into nonwoven fabric by hydroentanglement, which was then calendered at a temperature of 40° C. and a linear pressure of 250 kgf/cm. The calendered nonwoven fabric was soaked in a 0.05% aqueous solution of a surface active agent (Mydol 10 from Kao Corp.) and dried spontaneously to give a test nonwoven fabric.

The resulting test nonwoven fabric was analyzed for pore size distribution in accordance with the method described above to find that the proportion of pores of 6 μm or smaller was 40%. A sanitary napkin was made in the same manner as in Example 1, except for using the resulting test nonwoven fabric as a blood separating member.

Comparative Example 1

A nonwoven fabric having a basis weight of 60 g/m² was formed by melt blowing polypropylene (PP). The nonwoven fabric was soaked in a 0.05% aqueous solution of a surface active agent (Mydol 10 from Kao Corp.) and dried spontaneously to give a test nonwoven fabric.

The resulting test nonwoven fabric was analyzed for pore size distribution in accordance with the method described above to find that the proportion of pores of 6 μm or smaller was 14%. A sanitary napkin was made in the same manner as in Example 1, except for using the resulting test nonwoven fabric in place of that used in Example 1.

Comparative Example 2

A commercially available spunbonded nonwoven fabric (Syntex PS-112 available from Mitsui Chemical, Inc.) was soaked in a 0.05% aqueous solution of a surface active agent (Mydol 10 from Kao Corp.) and dried spontaneously to give a test nonwoven fabric. The resulting test nonwoven fabric was analyzed for pore size distribution in accordance with the method described above to find that the proportion of pores of 6 μm or smaller was 10%. A sanitary napkin was made in the same manner as in Example 1, except for using the resulting test nonwoven fabric in place of that used in Example 1.

Evaluation of Resistance to Rewet

The sanitary napkins prepared in Examples 1 to 3 and Comparative Examples 1 and 2 were tested in accordance with the rewet test method described below to evaluate resistance to rewet. The results obtained are shown in Table 1 below.

Rewet Test Method

An acrylic resin plate having a 10 mm diameter opening was placed on the sanitary napkin with the opening at the center of the topsheet. Weights were put on the acrylic resin plate to give a pressure of $3.5 \times 10^2$ Pa to the sanitary napkin. In this state, 3 g of defibrinated horse blood was poured through the opening of the plate. One minute later, the plate was removed, and a stack of ten 6 cm wide and 10 cm long sheets of tissue paper was put on the topsheet. Weights were put thereon to apply a pressure of $6.6 \times 10^3$ Pa. After 2-minute pressure application, the mass of the blood absorbed by the tissue paper was measured, which was taken as an amount of rewet.

TABLE 1

|  | Example 1 | Example 2 | Example 3 | Comp. Example 1 | Comp. Example 2 |
|---|---|---|---|---|---|
| Proportion of pores of 6 μm or smaller (%) | 20 | 20 | 40 | 14 | 10 |
| Intermediate sheet | no | yes | no | no | no |
| Amount of rewet (g) | 0.17 | 0.15 | 0.17 | 0.6 | 0.9 |

As is seen from Table 1, the sanitary napkins of Examples show appreciably reduced rewet as compared with those of Comparative Examples.

Comparative Example 4

A nonwoven fabric having an average fiber diameter of 10 μm and a basis weight of 60 g/m² was formed by melt blowing polypropylene (PP). The resulting nonwoven fabric was calendered at a temperature of 40° C. and a linear pressure of 250 kgf/cm and then soaked in a 0.05% aqueous solution of a surface active agent (Mydol 10 from Kao Corp.) and dried spontaneously to give a test nonwoven fabric.

The resulting test nonwoven fabric having a basis weight of 60 g/m² was analyzed for pore size distribution in accordance with the method described above to find that the proportion of pores of 6 μm or smaller was 20%. The test nonwoven fabric was cut into a 7 cm wide and 15 cm long piece, which was used as a blood separating member.

Separately, an absorbent core (7 cm wide and 15 cm long) was prepared by spreading 1.0 g of superabsorbent polymer particles (EQ5 from Kao Corp.) on an air-through nonwoven fabric having a basis weight of 30 g/m² and composed of two layers; 20 g/m² of an upper layer made of core/sheath conjugate fibers having polyethylene terephthalate (PET) as a core and a mixture of 6 dtex polyethylene and 6 dtex PET as a sheath and 10 g/m² of a lower layer made of core/sheath conjugate fibers having a fineness of 2 dtex and composed of PET as a core and PE as a sheath. The superabsorbent polymer content was 76% based on the mass of the absorbent core.

A sanitary napkin was made by interposing the resulting blood separating member and absorbent core between the topsheet and backsheet taken out of a commercially available sanitary napkin (Laurier Sarasara Cushion (for day use) available from Kao Corp.). The blood separating member was on the topsheet side, with the absorbent core on the backsheet aide. The bonding between the blood separating member and the absorbent core and the bonding between the topsheet and the blood separating member were carried out with a solvent type adhesive (from Sumitomo 3M, Ltd.). An adhesive was not applied between the absorbent core and the backsheet.

Example 5

A sanitary napkin was made in the same manner as in Example 4, except for using an absorbent core having a basis weigh of 350 g/m² which was prepare by wrapping a mixed airlaid fiber aggregate composed of 240 g/m² of pulp and 95 g/m² of a superabsorbent polymer in tissue paper.

Example 6

A sanitary napkin was made in the same manner as in Example 4, except for changing the superabsorbent polymer content from 76% by 56% by mass.

Example 7

A sanitary napkin was made in the same manner as in Example 4, except for changing the superabsorbent polymer content from 76% by 61% by mass.

Reference Example 1

A sanitary napkin was prepared in the same manner as in Example 4, except that the absorbent core was not disposed.

Comparative Example 3

A sanitary napkin was prepared in the same manner as in Example 4, except for replacing the blood separating member with a spunbonded nonwoven fabric made of polypropylene fibers (average fiber diameter: 15 μm; proportion of pores of 6 μm or smaller: 15%; a basis weight: 30 g/m$^2$) and having no blood separating ability.

Comparative Example 4

A sanitary napkin was made in the same manner as in Example 4, except that the blood separating member was not used.

Reference Example 2

A sanitary napkin was prepared in the same manner as in Example 4, except that the superabsorbent polymer particles were not spread in the preparation of the absorbent core.

Evaluation of Resistance to Rewet

The sanitary napkins prepared in Examples 4 to 7, Reference Examples 1 and 2, and Comparative Examples 3 and 4 were tested in accordance with the rewet test method described below to evaluate resistance to rewet. The results obtained are shown in Table 2 below.

Rewet Test Method

A sanitary napkin was placed on a horizontal plane. An acrylic resin plate having a 1 cm diameter opening was placed thereon, and weights were put on the acrylic resin plate to give a pressure of 3.5×10$^2$ Pa to the sanitary napkin. In this state, 6 g of defibrinated horse blood (from Nippon Biotest Laboratories inc.) was poured through the opening of the plate in about one second. One minute later, the plate was removed, and a stack of ten 7 cm wide and 8 cm long sheets of absorbent paper having a basis weight of 30 g/m$^2$ (commercially available tissue paper) was put on the napkin. Weights were put thereon to apply a pressure of 6.6×10$^3$ Pa. After 2-minute pressure application, the mass of the blood absorbed by the tissue paper was measured, which was taken as an amount of rewet.

having a 1 cm diameter opening was placed thereon, and weights were put on the acrylic resin plate to give a pressure of 3.5×10$^2$ Pa to the sanitary napkin. In this state, 6 g of defibrinated horse blood (from Nippon Biotest Laboratories inc.) was poured through the opening of the plate in about one second. One minute later, the plate was removed, and a stack of ten 7 cm wide and 8 cm long sheets of absorbent paper having a grammage of 30 g/m$^2$ (commercially available tissue paper) was put on the napkin. Weights were put thereon to apply a pressure of 6.6×10$^3$ Pa. After 2-minute pressure application, the mass of the blood absorbed by the tissue paper was measured, which was taken as an amount of rewet.

TABLE 2

| | | Absorbent Core | | | |
|---|---|---|---|---|---|
| | Blood Separating Member | Fiber | Super absorbent Polymer (EQ5) | Super absorbent Polymer Content (%) | Amount of Rewet (g) |
| Example No. 4 | Yes | PE/PET | yes | 76 | 1.0 |
| 5 | yes | Pulp | yes | 27 | 0.8 |
| 6 | yes | PE/PET | yes | 56 | 1.6 |
| 7 | yes | PE/PET | yes | 61 | 1.3 |
| Ref. Example 1 | yes | no | no | — | 2.2 |
| Comp. Example 3 | no | PE/PET | yes | 76 | 2.0 |
| Comp. Example 4 | no | PE/PET | Yes | 76 | 2.3 |
| Ref. Example 2 | yes | PE/PET | no | — | 2.2 | weight of 60 g/m$^2$ was formed by melt blowing polypropylene (PP). The resulting nonwoven fabric was calendered at a temperature of 40° C. and a linear pressure of 250 kgf/cm and then soaked in a 0.05% aqueous solution of a surface active agent (Mydol 10 from Kao Corp.) and dried spontaneously to give a test nonwoven fabric.

The resulting test nonwoven fabric was analyzed for pore size distribution in accordance with the method described above to find that the proportion of pores of 6 μm or smaller was 63%. The test nonwoven fabric was cut into pieces 7 cm wide and 15 cm long. Four of the cut pieces were stacked one on top of another to make a blood separating member stack. A sanitary napkin was made by interposing the resulting blood separating member stack between the topsheet and backsheet taken out of a commercially available sanitary napkin (Laurier Sarasara Cushion (for day use) available from Kao Corp.).

Example 9

A nonwoven fabric having a thickness of 0.8 mm and a basis weight of 40 g/m$^2$ was formed from 4 dtex core/sheath conjugate fibers having polypropylene as a core and a propylene-ethylene copolymer as a sheath by through-air bonding. The nonwoven fabric was cut to a width of 7 cm and a length of 15 cm to obtain an intermediate sheet. A sanitary napkin was prepared in the same manner as in Example 8, except for interposing the intermediate sheet and the same blood separating member stack as used in Example 8 between the topsheet and the backsheet, with the intermediate sheet on the topsheet side, and the blood separating member stack on the backsheet side.

Example 10

A sanitary napkin was made in the same manner as in Example 8, except that the blood separating member stack was drilled to form through-holes with an opening diameter of 1.5 mm at a spacing of 2 mm.

Reference Example 3

A test nonwoven fabric having a basis weight of 240 g/m$^2$ and a proportion of pores of 6 μm or smaller of 63% was prepared in the same manner as in Example 8, except for changing the weight of the melt-blown nonwoven fabric. A sanitary napkin was obtained in the same manner as in Example 8, except for interposing the resulting test nonwoven fabric between the topsheet and the backsheet.

Comparative Example 5

A spunbonded nonwoven fabric made of polypropylene fibers (average fiber diameter: 15 μm; proportion of pores of 6 μm or smaller: 15%; a basis weight: 30 g/m$^2$) and having no blood separating ability was prepared. Eight pieces (7 cm wide and 15 cm long) cut out of the resulting nonwoven fabric were stacked one on top of another. A sanitary napkin was made in the same manner as in Example 8, except for replacing the blood separating member stack as used in Example 8 with the resulting stack.

Evaluation

A sanitary napkin was placed horizontally. An acrylic resin plate having a 1 cm diameter opening and weights were placed thereon to apply a load of 3.6 g/cm$^2$ to the sanitary napkin. 6 g of defibrinated horse blood was poured through the opening of the plate in about one second, and the time required for the blood to be absorbed completely was measured. After the absorption, the test system was left to stand for one minute, and the plate and weights were removed. A stack of ten 7 cm wide and 10 cm long sheets of absorbent paper having a basis weight of 30 g/m$^2$ (commercially available tissue paper) was put on the napkin. Weights were put thereon to apply a pressure of 6.6×10$^3$ Pa. After 2-minute pressure application, the stack of absorbent paper was weighed. The amount of the blood absorbed by the tissue paper was obtained as a difference of weight between before and after absorption, which was taken as an amount of rewet. The results obtained are shown in Table 3.

TABLE 3

|  | Example 8 | Example 9 | Example 10 | Ref. Example 3 | Comp. Example 5 |
|---|---|---|---|---|---|
| Proportion of pores of 6 μm or smaller (%) | 63 | 63 | 63 | 63 | 15 |
| Number of blood separating members stacked | 4 | 4 | 4 | 1 | 8 |
| Time of absorption (sec) | 32 | 13 | 15 | 40 | 30 |
| Amount of rewet (g) | 0.1 | 0.1 | 0.1 | 2.0 | 0.7 |

As can be seen from the results in Table 3, the sanitary napkins of Examples 8 to 10 show markedly reduced rewet as compared with those of Comparative Example and Reference Example. On comparing Examples 9 and 10 with Example 8, it is proved that the absorption rate can be increased while suppressing rewet by providing an intermediate sheet or through-holes in the blood separating members.

Industrial Applicability

According to the present invention, rewet with menstrual blood (blood) is remarkably reduced.

The invention claimed is:

1. An absorbent article comprising a blood separating member capable of separating blood into blood cells and plasma, a liquid permeable topsheet, an intermediate sheet, and an absorbent core comprising a fiber aggregate and a superabsorbent polymer, wherein:
    the blood separating member has pores with a diameter of 6 μm or smaller in a proportion of from 20% to 90% in a pore size distribution measured in accordance with ASTM F361-86;
    the blood separating member is formed of nonwoven fabric obtained by calendering a fiber aggregate made by melt blowing or by using splittable fibers, wherein a calendering temperature is a softening point of fibers constituting the fiber aggregate or lower;
    the blood separating member is on a garment facing side of the topsheet, between the topsheet and the absorbent core;
    the intermediate sheet is between the topsheet and the blood separating member; and
    the blood separating member comprises a plurality of blood separating members stacked one on top of another, wherein at least one of the blood separating members has through-holes which penetrate a thickness thereof.

2. The absorbent article according to claim 1, wherein the blood separating member is formed of a porous film.

3. The absorbent article according to claim 1, wherein the stack of the blood separating members is on the garment facing side of the topsheet, and the intermediate sheet is between the topsheet and the stack.

4. The absorbent article according to claim 1, wherein at least one of the blood separating members is formed of a fiber aggregate made mainly of hydrophilic fibers.

5. The absorbent article according to claim 1, wherein the blood separating member is formed of nonwoven fabric obtained by calendering a fiber aggregate made by melt blowing.

6. The absorbent article according to claim 1, wherein the blood separating member is formed of nonwoven fabric obtained by calendering a fiber aggregate made by using splittable fibers.

7. The absorbent article according to claim 1, wherein the stack of the blood separating members is on the garment facing side of the topsheet, and the intermediate sheet is between the topsheet and the stack, and wherein at least one of the blood separating members is formed of a fiber aggregate made mainly of hydrophilic fibers.

8. The absorbent article according to claim 1, wherein the blood separating member does not have pores of 6 μm or smaller diameter in a proportion of 100%.

9. The absorbent article according to claim 1, wherein an absorbent core is not present between the topsheet and the intermediate sheet.

10. The absorbent article according to claim 1, wherein the through-holes have an opening diameter of 1 to 3 mm.

* * * * *